United States Patent [19]

Holcomb

[11] 4,426,141

[45] Jan. 17, 1984

[54] BRIGHT RING KERATOSCOPE

[76] Inventor: Harry F. Holcomb, 4501 Mission Bay Dr., San Diego, Calif. 92100

[21] Appl. No.: 256,754

[22] Filed: Apr. 23, 1981

[51] Int. Cl.³ .......................... A61B 3/10; A61B 3/00
[52] U.S. Cl. ..................................... 351/212; 351/247
[58] Field of Search .......................... 351/6, 13, 14, 16

[56] References Cited

U.S. PATENT DOCUMENTS 2,016,780 10/1935 Hartinger
3,248,162 4/1966 Knoll
4,165,744 8/1979 Cravy et al. ............................ 351/13
4,172,639 10/1979 Lang et al. ............................. 351/13

Primary Examiner—John K. Corbin
Assistant Examiner—Rodney Bovernick
Attorney, Agent, or Firm—Karl W. Flocks; A. Fred Starobin

[57] ABSTRACT

A hand-held keratoscope designed to project a bright circular ring on the cornea having a circular glass ring attached to a handle by a retainer ring with the circular glass ring having a flat polished top surface and a frosted inward sloping bottom surface.

10 Claims, 5 Drawing Figures

BRIGHT RING KERATOSCOPE

BACKGROUND OF THE INVENTION

The present invention refers to a keratoscope which is an instrument for determining the symmetry of the curvature of the corona, for estimating the degree of astigmatism (corneal warpage) and the axis of astigmatism. More specifically, the instrument of the present invention can be used during surgery on the eye, in lieu of more expensive instruments which accomplish the same purpose but with less convenience.

The keratoscope is used with an operating microscope, which is now standard equipment for eye surgery. Its most common application is for monitoring corneal astigmatism during closure of the incision at the end of a cataract operation.

SUMMARY OF THE INVENTION

The present invention is a keratoscope usually used with a microscope for estimating the degree of astigmatism and the axis of astigmatism.

The present invention is used for eye surgery for monitoring corneal astigmatism during closure of an incision in the eye such as for example at the end of a cataract operation.

The present invention allows a surgeon to judge the accuracy of his closure with regard to placement and tension of the sutures and by controlling those parameters to reduce post-operative astigmatism in the patient's eye.

An object of the present invention is to have a keratoscope which requires no attachment to the microscope and is quite inexpensive.

A further object of the present invention is to have a reflecting type keratoscope which casts a sufficiently bright reflection to be useful in medical determinations.

Another object of the present invention is to have an instrument having versatility in that it can easily be moved from one area of the cornea to another to estimate astigmatism in specific places and closer or further from the cornea to change the amount of area measured.

Basically the present invention is a hand-held type of keratoscope or keratometer having a ring, preferably of glass, attached to a handle, with a flat polished top surface and a frosted inward sloping bottom surface.

BRIEF DESCRIPTION OF THE DRAWINGS

These as well as further advantages which are inherent in the invention will become apparent from the following description, reference being had to the accompanying drawings wherein.

DESCRIPTION OF A PREFERRED EMBODIMENT

Figure 1:
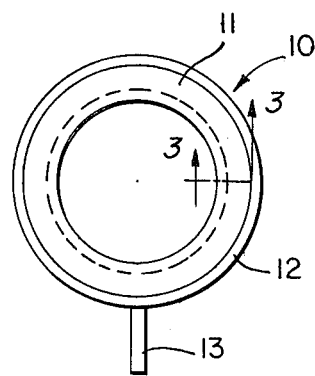
FIG. 1 is a top plan view of the keratoscope of the present invention when considered in the usual position of use during surgery.
Figure 4:
FIG. 4 is a top plan view of the image reflected on the cornea when the cornea is spherical.
Figure 5:
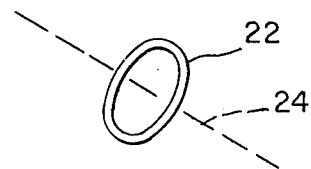
FIG. 5 is a view similar to that of FIG. 4 when testing an astigmatic cornea.

FIG. 1 shows a view from above or top plan view of the keratoscope or keratometer 10 of the present invention. Keratoscope 10 is also shown in a side elevational view in FIG. 2 as it is used positioned between a microscope and the cornea of the eye, which may be undergoing surgery. The light from the microscope will be caused by the keratoscope to reflect a bright ring on the cornea of the eye. Such bright rings may appear as shown in FIG. 4 or FIG. 5.

Keratoscope 10 is composed of a glass ring 11, held in a retaining ring 12, with a handle 13 attached to retaining ring 12.

The handle 13 should be of a material that will not tarnish with repeated autoclaving. Neither extreme hardness nor malleability are required.

Retaining ring 12 should be considered as part of the optical system of keratoscope 10. Its inside diameter must be as nearly circular and as nearly concentric with glass ring 11 as possible. Retaining ring 12 should fit glass ring 11 smoothly and snugly throughout its circumference.

Glass ring 11 should be made, as far as practical, of a glass that will not discolor with frequent autoclaving. A model was made from an optical flat (Edmond Scientific Company Stock #2084) and although it was found to yellow slightly in use, there was no degradation in its performance.

Figure 3:
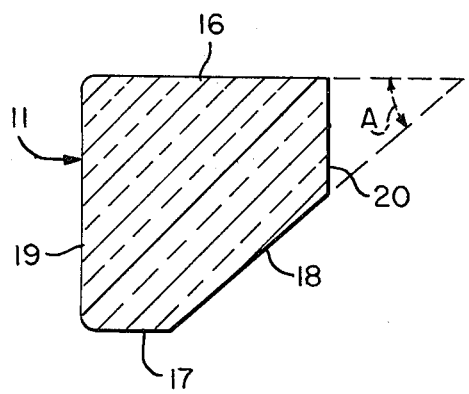
FIG. 3 is an enlarged cross-section along line 3—3 of FIG. 1.

A cross-sectioned view of glass ring 11 is shown in FIG. 3 taken along line 3—3 of FIG. 1. Top surface 16 and bottom surface 17 should be polished and flat. The beveled surface 18 should be ground and left unpolished. Surface 18 is therefore a frosted surface. Inner surface 19 should be left unpolished and outer surface 20 may also be left unpolished. The top and bottom edges bordering the inner surface 19 should be ground with a very slight bevel or rounded for the sake of durability and safety.

Specifications for the size of the glass ring 11 which have been found to work in a most preferred manner in keratoscope 10 are as follows. Glass ring 11 would preferably have an outside diameter of 20 mm and an inside diameter of 16 mm. Top surface 16 would have a length of 2 mm and inner surface 19 would also have a length of 2 mm. Bottom surface 17 has a length of 0.7 mm. These lengths are all measured along the edges shown in the cross-section view of FIG. 3. Angle A also shown in that figure, determining the bevel of glass ring 11 would in the case illustrated be approximately 40°. The use of an angle A in the range of 30 to 50 degrees also appears to give desired results with accompanying changes in dimensions. Such change of dimensions may advantageously narrow the width of the ring with the steeper angle of the bevel with a thin ring image, referring to the width of the edge of the image, found to be easier to interpret than a thicker ring image. Also, the use of ground glass has been found to be much better than plastic in the keratoscope of the present invention. The image projected when glass is used has been found to be much brighter than when plastic is used under the same circumstances. Also it has been found that the plastic is much more liable to develop scratches than when the device using glass is put in with other surgical instruments. Also when using glass there is less concern about distortion.

The outside diameter of the glass ring 11 may be increased as a means of decreasing its thickness at its outer circumference, if this is desirable to improve its fit into retaining ring 12.

The handle 13 should have sufficient weight so as to give a proper "feel" for the surgeon or other user.

Figure 2:
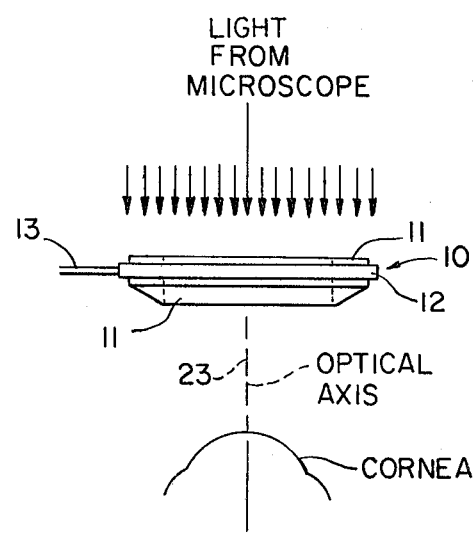
FIG. 2 is a side elevation of the keratoscope shown in use relative to a cornea.

The main purpose of the keratoscope of the present invention is to allow a surgeon who is operating on an eye, possibly in a cateract operation, to monitor the corneal astigmatism during closure of the incision at the end of a cataract operation and to estimate the direction and degree of corneal astigmatism remaining after closure of the incision. In use, a microscope with coaxial illumination is required. The microscope is aligned with the optical axis of the eye and with illumination therefrom so aligned as shown in FIG. 2. The keratoscope 10 is introduced between the eye and the microscope so that its axis also coincides with that of the eye. The distance of keratoscope 10 from the cornea can be adjusted to provide the desired size of reflected bright ring 21 or 22 in the cornea. Examples of bright rings 21, 22 are shown in FIGS. 4 and 5 respectively. The polished top surface 16 of keratoscope 10 should face the microscope. Keratoscope 10 should be held with its plane perpendicular to the axis 23 of the eye and microscope. This is accomplished when the microscope illumination is reflected from polished surface 16 of keratoscope 10 into the observer's eyes through the microscope. The small amount of light thus reflected does not interfere with observation of the eye or cause any significant discomfort to the observer. The microscope light illuminates the frosted surface 18 of glass ring 11 which is reflected by the cornea to the eye of the observer through the microscope. If the cornea is spherical indicating no astigmatism, then the ovserver will see a bright, perfectly circular ring 21 as shown in FIG. 4, reflected from the cornea. This is determined by the judgement of the observer. By moving keratoscope 10 further from the cornea, the reflection 21 can be made to occupy only the center of the cornea, which is the most important area for visual purposes. On the other hand, moving keratoscope 10 closer to the cornea will provide a larger ring, making the estimation of its circularity somewhat easier.

The astigmatic cornea will present oval reflection 22 as shown in FIG. 5. The axis 24 through the shortest diameter of oval 22 represents the most positive axis of astigmatism. If overly tight sutures are the cause of the astigmatism, the flattest side of the oval, i.e., the axis 24 of the shortest diameter of the oval, will point toward the center of maximum suture tightness. The degree or amount of flattening indicates the degree or amount of astigmatism. The axis of least corneal curvature coincides with the longest axis of reflected oval 22. To correct this cause of astigmatism at the time of surgery, the surgeon must adjust the sutures in that median.

With the keratoscope of the present invention a resolution up to ± one diopter of astigmatism has been obtained. It is essential that the intraocular pressure be restored to normal before attempting to correct the astigmatism with this instrument, and this requires a water-tight wound closure of a type which can be readily adjusted. It has been found advisable to leave one or two diopters of positive astigmatism in the vertical meridian after final closure of the incision with 10-0 nylon suture material. This amount of astigmatism appears to disappear spontaneously within a week or two.

It will be obvious to those skilled in the art that various chages may be made without departing from the scope of the invention and the invention is not to be considered limited to what is shown in the drawings and described in the specification.

I claim:

1. A device for judging corneal astigmatism comprising
    a retaining means,
    a transparent ring held in said retaining means and including
        a flat polished top surface,
        inner and outer surfaces depending from opposite edges of said top surface,
        and a beveled unpolished surface on the opposite surface from said top surface.

2. The device of claim 1, further characterized by said transparent ring further including
    a flat polished bottom surface parallel to said top surface and connected to said beveled surface.

3. The device of claim 1, further characterized by said beveled surface being a frosted surface.

4. The device of claim 1, further characterized by said inner surface being an unpolished surface.

5. The device of claim 1, further characterized by said outer surface being an unpolished surface.

6. The device of claim 1, further characterized by said beveled surface being at an angle of substantially 30 to 50 degrees with said top surface.

7. The device of claims 1, 2, 3, 4, 5 or 6, further characterized by
    said transparent ring being a glass ring.

8. The device of claim 1, further characterized by said retaining means including
    a retainer ring fitted around said outer surface of said transparent ring,
    and holding means on said retainer ring.

9. The device of claim 8, further characterized by said holding means being a handle extending from said retainer ring.

10. A device for judging corneal astigmatism in conjunction with a microscope comprising
    a transparent circular ring and means to hold said circular ring, said ring including
    a polished top surface,
    inner and outer surfaces depending from opposite sides of said top surface,
    and an unpolished surface on the opposite surface from said top surface.

* * * * *